United States Patent
Prest et al.

(10) Patent No.: US 10,580,632 B2
(45) Date of Patent: Mar. 3, 2020

(54) IN-SITU CONDITIONING IN MASS SPECTROMETRY SYSTEMS

(71) Applicant: Agilent Technologies, Inc., Santa Clara, CA (US)

(72) Inventors: Harry F. Prest, Mountain View, CA (US); Charles W. Russ, IV, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/846,158

(22) Filed: Dec. 18, 2017

(65) Prior Publication Data
US 2019/0189413 A1 Jun. 20, 2019

(51) Int. Cl.
H01J 49/10 (2006.01)
H01J 49/00 (2006.01)
G01N 30/72 (2006.01)

(52) U.S. Cl.
CPC ...... *H01J 49/0031* (2013.01); *G01N 30/7206* (2013.01); *H01J 49/10* (2013.01)

(58) Field of Classification Search
USPC ....................................... 250/282
See application file for complete search history.

(56) References Cited

U.S. PATENT DOCUMENTS

| | | | |
|---|---|---|---|
| 4,833,319 A | 5/1989 | Knauer | |
| RE33,344 E | 9/1990 | Stafford | |
| 4,994,096 A | 2/1991 | Klein et al. | |
| 5,491,337 A | 2/1996 | Jenkins et al. | |
| 5,830,353 A | 11/1998 | Henderson | |
| 5,942,752 A | 8/1999 | Wang | |
| 6,808,933 B1 | 10/2004 | Prest | |
| 7,138,642 B2 | 11/2006 | Hieke | |
| 7,264,677 B2 | 9/2007 | Nakahara et al. | |
| 7,276,688 B2 | 10/2007 | Weiss | |
| 7,304,299 B2 | 12/2007 | Perkins | |
| 7,399,958 B2 | 7/2008 | Miller et al. | |
| 7,482,584 B2 | 1/2009 | Kämpf et al. | |
| 7,642,510 B2 | 1/2010 | McEwen | |
| 7,812,307 B2 | 10/2010 | Dutton et al. | |
| 7,836,450 B2 | 11/2010 | Kissell | |
| 7,836,750 B2 | 11/2010 | Heuvel et al. | |
| 7,838,842 B2 * | 11/2010 | Horsky | C23C 14/48 250/423 R |
| 7,928,370 B2 | 4/2011 | Amirav et al. | |
| 8,003,959 B2 * | 8/2011 | Platow | H01J 27/02 134/1.1 |
| 8,210,026 B2 | 7/2012 | Klee et al. | |
| 8,237,134 B2 * | 8/2012 | Kaim | H01J 37/08 250/492.21 |

(Continued)

OTHER PUBLICATIONS

"Agilent JetClean for OpenLAB". Accessed Sep. 26, 2017.
(Continued)

*Primary Examiner* — Phillip A Johnston

(57) ABSTRACT

In a mass spectrometer or gas chromatograph/mass spectrometer system, one or more different conditioning gases are added to condition or modify one or more surfaces or regions of the ion source. The conditioning gas(es) may be added directly into the ion source. The conditioning gas may be added off-line, when the mass spectrometer is not analyzing a sample.

20 Claims, 4 Drawing Sheets

(56) References Cited

U.S. PATENT DOCUMENTS

| | | |
|---|---|---|
| 8,378,293 B1 * | 2/2013 | Quimby .............. H01J 49/0027 |
| | | 250/282 |
| 8,513,593 B2 | 8/2013 | Quimby et al. |
| 8,603,252 B2 * | 12/2013 | Dimeo .................. C23C 14/564 |
| | | 134/1.1 |
| 2003/0160168 A1 | 8/2003 | Speakman et al. |
| 2007/0075240 A1 | 4/2007 | Hieke |
| 2007/0114438 A1 | 5/2007 | Holle et al. |
| 2007/0176092 A1 | 8/2007 | Miller et al. |
| 2007/0224693 A1 | 9/2007 | Prest |
| 2008/0083874 A1 | 4/2008 | Prest et al. |
| 2008/0185512 A1 | 8/2008 | Miller et al. |
| 2009/0014644 A1 | 1/2009 | Yang et al. |
| 2009/0194679 A1 | 8/2009 | Doherty et al. |
| 2010/0154835 A1 | 6/2010 | Dimeo et al. |
| 2011/0108058 A1 * | 5/2011 | Srivastava .............. H01J 37/08 |
| | | 134/1.1 |
| 2012/0048310 A1 | 3/2012 | Maekawa |
| 2013/0099113 A1 | 4/2013 | Quimby et al. |
| 2014/0199492 A1 * | 7/2014 | Matsumoto ........... C23C 14/564 |
| | | 427/523 |

OTHER PUBLICATIONS

Extended European Search Report issued in counterpart EP Application No. 18211505.5 dated May 13, 2019 (twelve (12) pages).
Prest, Harry. "Agilent JetCLean: In-situ GC/MS Ion Source Cleaning and Conditioning." Accessed Aug. 15, 2016.

* cited by examiner

IN-SITU CONDITIONING IN MASS SPECTROMETRY SYSTEMS

TECHNICAL FIELD

The present invention relates generally to mass spectrometry, including mass spectrometry coupled with chromatography. More particularly, the invention relates to conditioning an ion source of a mass spectrometer to improve or restore its performance.

BACKGROUND

A mass spectrometer (MS) generally includes an ion source for producing charged species from an introduced sample, a mass analyzer for separating the charged species according to their mass-to-charge ratios (m/z ratios, or simply "masses"), and an ion detector for counting the separated species to provide electrical signals from which mass spectra may be produced. The sample may be introduced into the ion source by various techniques. In one example, a gas chromatograph (GC) is interfaced with the MS such that the sample output from the GC column—containing chromatographically separated sample components (e.g., chemical compounds)—serves as the sample input into the ion source. The latter system is often termed a GC/MS system.

As an MS continues to be operated over time, invariably some alteration or degradation in the performance of the MS, particularly the ion source, occurs due to the samples, their matrix (e.g., heavy hydrocarbons in petroleum samples, triglycerides in fat samples, etc.) and solvents, stationary phase bleed from the GC column, or other recalcitrant substances, all of which may accumulate over time. Even at the initial operation of the MS, the MS may not be stabilized or "conditioned" to provide adequate or uniform performance. In the case of gas chromatography where an electron impact (EI) or chemical ionization (CI) source is typically utilized in the MS, the ion source can be rapidly fouled by the introduced sample components, which results in degraded performance as seen in the analyte signal or spectral characteristics. Another problem, especially with high-boiling analytes, is that peak tailing can increase with continued use in addition to reduced signal response. The degraded performance may be manifested in many ways, but typically the metrics are reduced analyte signal response and high system background noise, the latter being particularly troublesome for analyte detection and identification.

These problems have conventionally required that the MS be cleaned periodically. Generally, the higher the rate of contaminant deposition, the more often the MS must be cleaned. The common, conventional solution has been to vent the MS system, remove the critically affected components (e.g., ion source, ion optics, pre-filter, etc.), treat the removed components to mechanical and/or chemical cleaning followed by other processes (e.g., muffle or vacuum furnace baking), and then re-install the components in the MS system. Such conventional ex situ cleaning procedures can be quite complex and lengthy procedures, involving potentially toxic solvents, expensive equipment, and the time and care of skilled technicians. Moreover, the cleaning process only temporarily solves the problem. After performing an iteration of cleaning and resuming the analytical operation of the MS, the performance of the MS will start to degrade again, eventually requiring another iteration of cleaning. In addition, the conventional cleaning process may fail due to mechanical issues associated with the reinstallation of components, or because some step in the procedure was compromised (e.g., a cleaning solvent was contaminated). Such failures may not be discovered until the MS is reassembled, under vacuum, and at operating conditions. Also, the process of venting entrains certain background species, the most abundant of which is water, which results in additional time being required to eliminate these substances. Water as a contaminant can cause a rapid reduction in MS signal response.

U.S. Pat. Nos. 8,378,293 and 8,513,593, the entire contents of which are incorporated by reference herein, describe apparatuses and methods entailing the addition of a conditioning gas (or conditioning agent) to a mass spectrometry (MS) system to condition (or re-condition) the MS system in situ so as to improve or restore its performance. Hydrogen in particular was found to be highly effective as a conditioning agent in an MS environment. Hydrogen rapidly diffuses and displaces surface contaminants. Hydrogen when dissociated or in higher excited, meta-stable or pseudo-Rydberg states (such as by electron impact or other processes) is very active and can reduce many adsorbed compounds, such as those that tend to become adsorbed on ion source surfaces and degrade operation. Moreover, hydrogen can alter metal oxidation states. The metal surfaces of an MS system are known to participate in a variety of reactions that affect the analytes and other introduced compounds, such as dehydration or reduction as occur in the ion source. By converting the metals from a range of oxidation states to a reproducible and fixed set, performance can be made more consistent. In the case of the ion source, spectral characteristics can be greatly stabilized.

More recently, however, it has further been found that conditioning the MS system with hydrogen can be more favorable or less favorable for compound analysis by the MS system, depending on compounds themselves and the state of the MS system (e.g., the ion source) before and/or after treatment with hydrogen. That is, in some situations conditioning with hydrogen, or at least with hydrogen alone, may have adverse effects on the analysis of a given compound.

In view of the foregoing, there is an ongoing need in mass spectrometry, including chromatography/mass spectrometry, for further improvements in methods and apparatuses for conditioning an MS system. There is also a need for further improvements in methods and apparatuses for in situ conditioning that is carried out at the MS system, whereby the need for conventional ex situ cleaning is eliminated or at least significantly reduced and/or simplified.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for operating a mass spectrometer (MS) system includes: flowing a first conditioning gas into an ion source of the MS system without introducing a sample into the ion source; ionizing the first conditioning gas, wherein the ion source is conditioned by the first conditioning gas; after flowing the first conditioning gas, flowing a second conditioning gas into the ion source without introducing a sample into the ion source; after flowing the first conditioning gas, flowing a second conditioning gas into the ion source without introducing a sample into the ion source; ionizing the second conditioning gas, wherein the ion source is conditioned by the second conditioning gas; and after flowing the second conditioning gas, analyzing a sample by introducing the sample into the conditioned ion source and collecting analytical data from the sample, wherein: the first conditioning gas has a composition comprising at least 90% hydrogen gas by volume; and the second conditioning gas has a composition comprising from 0% to less than 90% hydrogen gas by volume.

According to another embodiment, a method for operating a mass spectrometry (MS) system includes: flowing a first conditioning gas into an ion source of the MS system without introducing a sample into the ion source; ionizing the first conditioning gas, wherein the ion source is conditioned by the first conditioning gas; after flowing the first conditioning gas, flowing a second conditioning gas into the ion source without introducing a sample into the ion source; ionizing the second conditioning gas, wherein the ion source is conditioned by the second conditioning gas; and after flowing the second conditioning gas, analyzing a sample by introducing the sample with a carrier gas into the conditioned ion source and collecting analytical data from the sample, wherein: the carrier gas has a composition comprising at least 90% hydrogen gas by volume; the first conditioning gas has a composition comprising from 0% to less than 90% hydrogen gas by volume; and the second conditioning gas has a composition comprising from 0% to less than 90% hydrogen gas by volume, and is different from the first conditioning gas.

According to another embodiment, a mass spectrometry (MS) system is configured for performing any of the methods disclosed herein.

In some embodiments, the MS system may be a chromatography/mass spectrometry system providing chromatographically separated sample analytes to the mass spectrometer, such as a gas chromatography/mass spectrometry (GC/MS) system that includes a gas chromatograph.

According to another embodiment, a non-transitory computer-readable medium is provided that includes instructions stored thereon, that when executed on a processor, control or perform all or part of any of the methods disclosed herein.

According to another embodiment, a mass spectrometry (MS) system is provided that includes the computer-readable medium.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
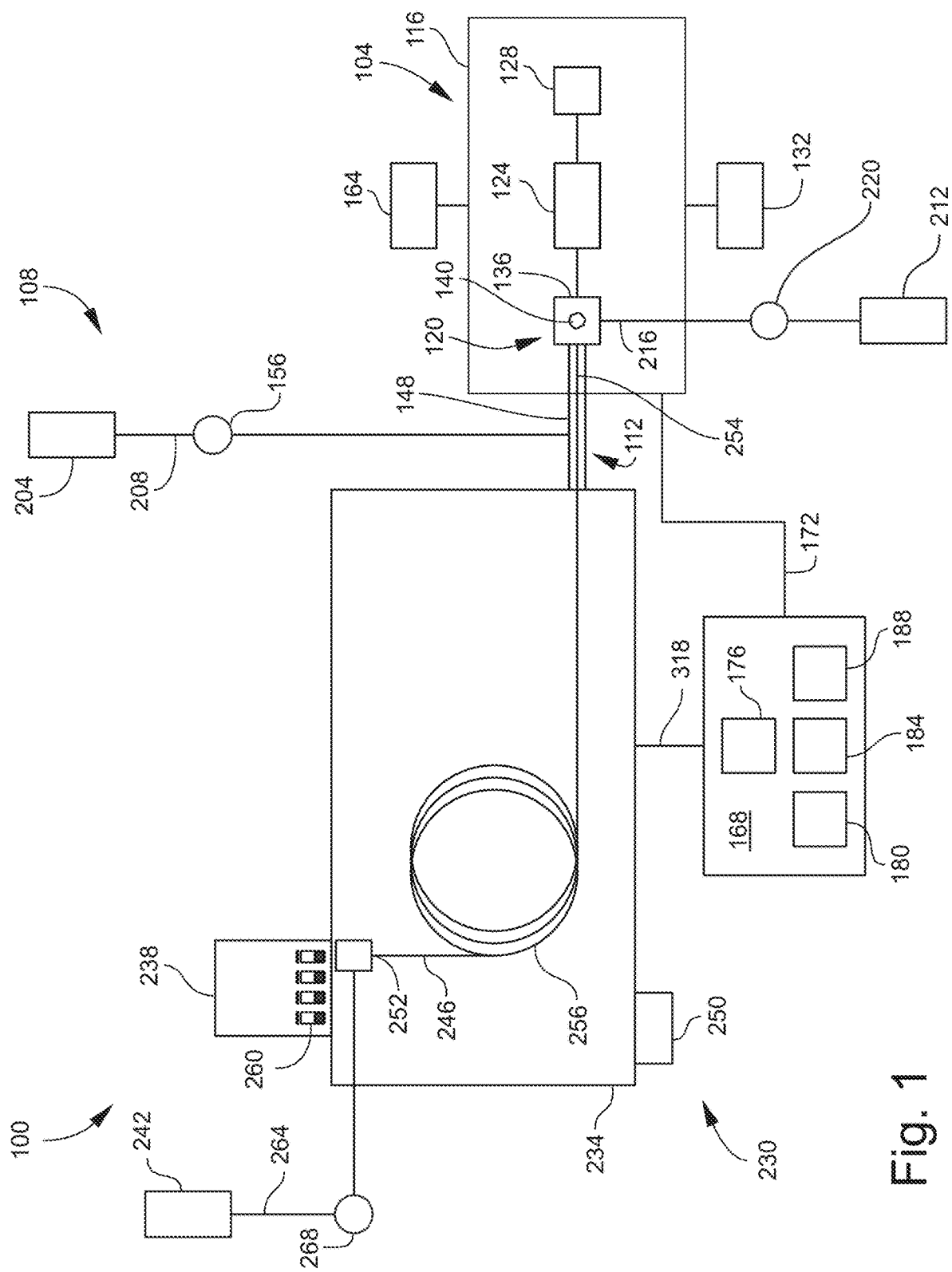
FIG. 1 is a schematic view of an example of a mass spectrometry (MS) system according to an embodiment of the present disclosure.

As used herein, the term "mass spectrometry system" (or "MS system") refers to a system that includes a mass spectrometer with or without a chromatograph being operatively interfaced with the mass spectrometer. Thus, for convenience the term "MS system" may also encompass (or be used interchangeably with) the term "chromatograph/mass spectrometry system," including the term "gas chromatograph/mass spectrometry system" (or "GC/MS system"), depending on the particular embodiment of interest.

In the context of the present disclosure, the term "analyte" refers generally to any sample molecule of interest to a researcher or user of an MS system—that is, a molecule on which an analysis is desired such as, for example, a chromatographic, mass spectral, or chromatographic/mass spectral analysis. The term "sample" or "sample matrix" refers to any substance known or suspected of containing analytes. The sample may include a combination of analytes and non-analytes. The term "non-analytes" or "non-analytical components" in this context refers to components of the sample for which analysis is not of interest because such components do not have analytical value and/or impair (e.g., interfere with) the analysis of the desired analytes. Non-analytes may generally be any molecules not of interest such as contaminants or impurities, or delivered by a chromatographic system (e.g., the effluent column phase). Examples of non-analytes may include, but are not limited to, water, oils, solvents, environmental solids (e.g., sediment or soil) or liquids, biologicals (e.g., urine, blood, tissue, etc.), foodstuffs, agricultural samples (e.g., vegetables, processed or unprocessed meats, etc. or other media in which the desired analytes may be found, as well as stationary phase material that has bled from a chromatographic column. The source of non-analytes may be the sample being analyzed at the time of operating an MS system to acquire analytical data on the sample. Alternatively or additionally, non-analytes may be residual species already present in the mass spectrometer prior to operating the MS system to acquire analytical data at a given time, such residual species having accumulated as a result prior use(s) of the MS system.

For purposes of the present disclosure, the term "analyte" also refers to compounds that may be analyzed by the MS system for the purpose of providing a reference, standard, tuning vehicle, or calibrant.

In the context of the present disclosure, the term "conditioning" generally refers to altering the surface chemistry of surfaces of an ion source to bring the ion source to a condition that improves or optimizes the performance of the ion source. In one aspect, conditioning is accomplished by operating an MS system to flow a conditioning gas into an ion source of the MS system, and ionizing the conditioning gas to thereby expose internal surfaces of the ion source to the ionized conditioning gas.

For purposes of the present disclosure, the term "gas" (e.g., conditioning gas) is taken to encompass the term "vapor." Examples of vapors include, but are not limited to, vapors obtained by distillation, or extraction from the headspace of a container, from a liquid.

The present disclosure describes various embodiments entailing the introduction of two or more different conditioning gases (or conditioning agents) into the ion source of a mass spectrometry (MS) system, as a mixture in a single step or individually (and/or as a mixture) in two or more steps, to condition (or re-condition) the ion source in situ so as to improve or restore its performance. Typically, the ion source to be conditioned is an electron ionization (EI) source, a chemical ionization (CI) source, or a photoionization (PI) source. While the conditioning gas is flowing into the internal volume (ionization chamber) of the ion source, and/or after the conditioning gas has flowed into the ionization chamber, the ion source is operated to apply energy (typically by generating electrons or photons) to the conditioning gas sufficient to ionize the conditioning gas, i.e. to create conditioning ions. Without wishing to be bound by any particular theory at the present time, the ionized conditioning gases may serve one or more of the following functions: conditioning (i.e., modifying the condition of) one or more surfaces of the ion source, such as by hydrogen reduction followed by polymerization; reducing or removing non-analytes such as matrix components that have accumulated in the ion source after sample analysis; accelerating the conditioning of the MS system after a vent/pump-down procedure; and restoring or creating an ion source condition (e.g., surface oxidation state or other surface metric) more optimal or consistent for MS analysis.

In situ treatment of an ion source using hydrogen has been shown to modify the condition inside the ion source. The post-treatment condition can be more favorable or less favorable for compound analysis depending on the compounds themselves and the state of the ion source before or after treatment. In the present context, the term "favorable" may refer to the ion source response for the compound, the peak shape of the compound produced by the ion source (e.g., the degree of peak tailing), the degree of degradation of the compound, or other metrics of analytical significance. However, it is possible that prolonged treatment by hydrogen can produce an ion source with a high degree of unfavorable features. The present disclosure proposes a second process, or one or more additional processes, effective to again alter the condition of the ion source to produce favored analytical performance. In this manner, the ion source activity may be controlled without removal of the ion source and bench processing. The goal is to improve stability, "activity", etc., for the analytes of interest in situ, knowing that the history of use of the ion source influences its pre-conditioning, post-conditioning, and operational states. Given this variability in initial states, multiple steps in conditioning allow greater flexibility in tailoring and recovering the ion source performance. Embodiments of the method disclosed herein may create a more consistent state for the ion source.

Generally, the conditioning gas may be any gas suitable for effectively performing a conditioning process in an ion source as described herein. Examples of conditioning gases (or vapors, depending on the particular example) include, but are not limited to, hydrogen, various hydrocarbons, ammonia, methylamine, various ketones, various alcohols, acetonitrile, silane ($SiH_4$), and silane derivatives (e.g., compounds having the general formula $Si_nH_{2n+2}$). Examples of hydrocarbons include, but are not limited to, methane, butane, isobutane, pentane, hexane, toluene, benzene, and xylene. Examples of ketones include, but are not limited to, acetone and similar compounds. Examples of alcohols include, but are not limited to, methanol and ethanol. The choice of conditioning gas(es) to be utilized may depend on a number of factors, for example the known or suspected composition of the sample to be analyzed after conditioning the ion source. The conditioning gas may be a single gas or a mixture of gases provided by gaseous or volatile liquid sources. In the present context, the term "gas" encompasses the term "vapor" as noted above.

The conditioning gas(es) may be added exclusively (without any other types of gases) depending on its nature and the specific state of the MS system. Alternatively, the conditioning gas(es) added to the ion source may be part of a blend (mixture) that includes a carrier gas and/or one or more other "auxiliary" gases. An auxiliary gas may generally be any inert gas that is different from the conditioning gas. Examples of auxiliary gases include, but are not limited to, helium, nitrogen, argon, and trace amounts of other gases (e.g., impurities) that may be present with the conditioning gas supplied to the MS system and have negligible or no effects on the conditioning process.

The conditioning gas is introduced directly into the ion source. For this purpose, the MS system may have a conditioning gas line dedicated to conducting the conditioning gas into the ion source. In some embodiments, the MS system is part of a hybrid gas chromatograph/mass spectrometer (GC/MS) system and thus is interfaced with a gas chromatograph (GC). In such embodiments, the conditioning gas may be routed through at least a part of the GC (e.g., the GC column) prior to being introduced into the MS system.

As described herein, the addition and ionization of conditioning gases are performed by operating the MS or GC/MS system in a conditioning mode. The conditioning mode is separate and distinct from the conventional analytical mode in which sample material is introduced into the ion source and ionized for the purpose of creating analyte ions that are subsequently analyzed by the mass analyzer of the MS system. That is, during the conditioning mode, a sample is not introduced into the ion source. Thus, the conditioning mode may be characterized as an "off-line" mode of operation of the MS system. In the off-line conditioning mode, the conditioning gas is introduced into the ion source and ionized for the purpose of creating conditioning ions that condition, or modify the surface chemistry of, internal surfaces of the ion source. The MS or GC/MS system may be configured to switch between the analytical mode and the conditioning mode. Execution of the switch from one mode to the other may be entirely or partially manual, or entirely or partially automated such as in response to evaluating one or more parameters as described further below. Generally, the conditioning gas may added during any stage of operation not involving the acquisition of analytical data on a sample, such as warm-up, tuning, pump-down, venting, cool-down, etc. Moreover, the off-line conditioning mode may entail adding the conditioning gas while one or more components (e.g., the ion source) of the MS or GC/MS system are removed.

The conditioning mode includes ionizing molecules of the conditioning gas while and/or after flowing the conditioning gas into the ionization chamber of the ion source. Depending on the type of ion source utilized, ionizing the conditioning gas may entail operating the ion source to emit electrons or photons into the ionization chamber. The presence of the electrons or photons enhances the conditioning process by one or more mechanisms, such as altering the surface chemistry of surfaces of the ionization chamber exposed to the energized conditioning gas. In addition to flowing the conditioning gas into the ion source, the conditioning mode may include maintaining the ion source at a desired temperature or within a desired temperature range. The conditioning process may be enhanced by heating the conditioning gas and/or the surfaces being treated by the conditioning gas.

In some embodiments, hydrogen may be utilized as a carrier gas for transporting a sample through a GC column instead of a more traditional carrier gas such as helium. The hydrogen carrier gas may be utilized as a conditioning gas when operating in the conditioning mode. In this case, the carrier gas source supplying the hydrogen may be utilized as a source of conditioning gas, which accordingly is conducted into the ion source of the mass spectrometer via the GC column and the sample interface between the GC and the ion source.

The conditions or parameters under which the conditioning gas is added may be controlled to enable the conditioning gas to effect conditioning in an optimized manner. As an example, the concentration of the conditioning gas in the ion source may be controlled, such as by regulating the flow rate of the conditioning gas into the ion source and/or diluting the stream of conditioning gas with an auxiliary gas as described above. Other conditions or parameters may include the temperature of the conditioning gas, and the temperature and/or pressure in the ion source.

FIG. 1 is a schematic view of an example of a mass spectrometer (MS) system 100. The MS system 100 may generally include a mass spectrometer 104 and a conditioning gas system 108. The mass spectrometer 104 may include a sample source, a sample (or sample/carrier gas) inlet or interface 112, an MS housing 116, an ion source (or ionization apparatus) 120, a mass analyzer 124, an ion detector 128, and a vacuum system 132.

The sample source may be any device configured for providing a quantity of sample material to the ion source 120 via the sample interface 112. As examples, the sample source may be associated with a batch volume, a sample probe, or a liquid or gas handling system. The flow of the sample material to the ion source 120 may be effected by any means, such as pumping, capillary action, or an electrically-assisted technique. In hyphenated techniques, the sample source may be associated with the output of an analytical separation instrument such as a gas chromatograph (GC) instrument, a liquid chromatographic (LC) instrument, a capillary electrophoresis (CE) instrument, a capillary electrochromatography (CEC) instrument, or the like. In some embodiments, the sample may be introduced or loaded directly into the ion source 120, without having to flow the sample from a sample source and through a column or conduit. In these embodiments, the sample inlet or sample interface to the ion source 120 may be, for example, a direct insertion probe. Depending on the technique employed to introduce the sample directly into the ion source, a carrier gas may or may not be utilized to assist in the sample introduction.

The ion source 120 may be any apparatus suitable for carrying out internal ionization to produce analyte ions from a sample stream received from the sample source and directing the as-produced ions into the mass analyzer 124. Additionally, in embodiments described herein, the ion source 120 is configured to create conditioning ions from a conditioning gas stream received from a conditioning gas source. For example, the ion source 120 may be an electron ionization (EI) source, a chemical ionization (CI) source, or a photoionization (PI) source. The ion source 120 may also include the capability of switching between modes of ionization. Generally, the ion source 120 includes an ionization chamber 136 and an ionization device 140. In the case of EI or CI, the ionization device 140 is an electron source such as a filament configured for emitting electrons in a manner understood by persons skilled in the art. In the case of PI, the ionization device 140 may be an ultraviolet (UV) lamp or other suitable photon source.

The mass analyzer 124 may be any device configured for separating, sorting or filtering analyte ions on the basis of their respective masses (i.e., mass-to-charge ratios, or m/z ratios). Examples of mass analyzers 124 include, but are not limited to, multipole electrode structures (e.g., mass filters, ion traps), time-of-flight (TOF) analyzers, electrostatic analyzers (ESAs), and magnetic sectors. The mass analyzer 124 may include a system of more than one mass analyzer, particularly when ion fragmentation is desired. As examples, the mass analyzer 124 may be a tandem MS or MS$^n$ system, as appreciated by persons skilled in the art. As another example, the mass analyzer 124 may include a mass filter followed by a collision cell or other ion fragmentation device, which in turn is followed by another mass filter or analyzer.

The ion detector 128 may be any device configured for collecting and measuring the flux (or current) of mass-discriminated ions outputted from the mass analyzer 124. Examples of ion detectors 128 include, but are not limited to, electron multipliers, micro-channel plates (MCPs), photomultipliers, and Faraday cups.

The ion source 120, mass analyzer 124, and ion detector 128 are disposed in the MS housing 116 with which the vacuum system 132 is interfaced. The MS housing 116 and vacuum system 132 are structured to define successive vacuum stages in the mass spectrometer 104. By this configuration, the ion source 120 and various regions of the mass analyzer 124 and ion detector 128 are maintained at desired vacuum levels. For this purpose, the vacuum system 132 typically includes one or more vacuum pumps that communicate with one or more vacuum stages via one or more exhaust ports of the MS housing 116.

The mass spectrometer 104 may also include a heating system 164. The heating system 164 may include one or more heating devices configured for controlling the respective temperatures of one or more components of the mass spectrometer 104, such as the sample interface 112, ionization chamber 136, mass analyzer 124, and ion detector 128. A given heating device may be configured for direct heating such as a resistive heating element, or indirect heating such as system for routing a heat exchanging medium.

The MS system 100 may also include a system controller (or system control module) 168. The system controller 168 may be configured for controlling and/or monitoring various aspects of the MS system 100, such as sample introduction into the ionization chamber 136, sample ionization, selection of modes of ionization, vacuum and pressure settings, temperature settings or varying temperature profiles implemented by the heating system 164, operating parameters of the mass analyzer 124 (e.g., applied electric and/or magnetic fields, collision/background gas introduction, timing of ion optics, and the like), acquisition and analysis of signals from the ion detector 128, generation and display of mass spectra or chromatograms, and so on as understood by persons skilled in the art. In particular, the system controller 168 may be configured for controlling and/or monitoring the selection of conditioning gases, introduction of conditioning gas(es) into the ion source 120, and ionization of the conditioning gas(es). For these purposes, the system controller 168 is schematically illustrated as being in signal communication with the mass spectrometer 104 via a communication link 172. The communication link 172 may be representative of several communication links respectively interfacing with various components of the MS system 100. A given communication link may be wired or wireless. Also for these purposes, the system controller 168 may include one or more types of hardware, firmware and/or software, as well as one or more types of memory. In the illustrated example, the system controller 168 includes an electronic processor 176, a database 180 stored in memory, a gas flow controller or control unit 184, and a performance evaluator or evaluation unit 188, as described further below. The system controller 168 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by the electronic processor 176 and/or software, and devices for loading media readable by the electronic processor 176 (e.g., logic instructions embodied in software, data, and the like). The system controller 168 may include an operating system (e.g., Microsoft Windows® software) for controlling and managing various functions of the system controller 168. One or more components of the system controller 168 may be located remotely from the MS system 100 and communicate with the local portion of the system controller 168 over a wired or wireless communication link. In some embodiments, the system controller 168 may include or be part of a laboratory information management system (LIMS), e.g., as may be utilized in a hospital or other medical setting.

The conditioning gas system 108 is configured for directing a conditioning gas, having a composition as described above, into the ion source 120. For this purpose, the conditioning gas system 108 may include one or more conditioning gas sources in communication with one or more conditioning gas lines, and one or more gas flow controllers as appropriate. The conditioning gas system 108 is configured for directing the conditioning gas(es) to the ion source 120. In one embodiment, a conditioning gas source 212 and an associated conditioning gas line 216 communicate directly with the ion source 120. The flow of the conditioning gas may be controlled by any means, such as a gas flow controller (or flow control module) 220 in operative communication with the conditioning gas line 216 and configured to regulate volumetric or mass flow rate of the conditioning gas. The flow controller 220 may, for example, include one or more valves, restrictors, mass flow controllers, pressure regulators, or the like. The flow controller 220 may be manually or electronically controlled. In some embodiments, the flow controller 156 may be a programmable electronic pneumatic controller (EPC) of known design and operation. In another embodiment, a conditioning gas source 204 and an associated conditioning gas line 208 communicate with a conduit 148 surrounding or adjacent to the sample interface 112 just upstream of the ion source 120, as may be regulated by a flow controller 156. In all such embodiments, the conditioning gas is introduced into the ion source 120.

At any given time during the conditioning mode, the conditioning gas system 108 may supply a single type of conditioning gas, or may include supply a blend (mixture) of two or more different types of conditioning gases. Thus, the conditioning gas sources 212 and 204 may represent sources of two or more different conditioning gases. The conditioning gas sources 212 and 204 and any associated gas flow controllers 220 and 156 may be manually operated and/or controlled by the system controller 168, such as by the gas flow controller 184 of the system controller 168, which may be in accordance with non-transitory computer-executable instructions.

In all of the foregoing embodiments, the conditioning gas system 108 provides a conditioning gas flow path from the conditioning gas source(s) 212 and/or 204, through the conditioning gas line(s) 216 and/or 208, and into the ion source 120. The conditioning gas flow path runs either directly into the ion source 120 or from a location upstream of the ion source 120.

FIG. 1 also illustrates an embodiment in which the MS system 100 includes a gas chromatograph (GC, or GC system) 230, in which case the MS system 100 may be characterized as being a gas chromatograph/mass spectrometry (GC/MS) system. In such an embodiment, the input end of the MS system 100 is interfaced with the GC 230 via the sample interface 112, which in this case may be termed a GC/MS interface. The GC 230 may generally include a GC housing 234, a sample introduction device 238 typically mounted at the GC housing 234, a carrier gas source 242, a GC column 246 disposed in the GC housing 234, and a heating device 250.

The column 246 includes a column inlet 252 communicating with the sample introduction device 238 via a sealed fluid connector, and a column outlet 254 communicating with the ionization chamber 136. A portion of the column 246 may extend through the sample interface 112 and into the ionization chamber 136, such that the column outlet 254 is located in the ionization chamber 136. Alternatively or equivalently, the column 246 may be coupled to a transfer line via a sealed fluid connector, in which case the transfer line extends through the sample interface 112 and into the ionization chamber 136. The column 246 includes a stationary phase, which typically comprises a liquid or polymer held on a solid support or film lining the inside wall of the column 246. To conserve space while maintaining a desired length, the column 246 may include a coiled section 256.

The sample introduction device 238 typically includes a device for injecting the sample into the column inlet 252, and may include a device for vaporizing the sample. The sample may be a matrix that includes sample material to be analytically separated in the column 246 and one or more solvents. The sample introduction device 238 may be configured to receive one or more sample containers 260, and may include a device (e.g., a carousel) for selecting a desired sample for injection into the column 246.

The carrier gas source 242 may communicate with the column inlet 252 via a carrier gas line 264. The carrier gas line 264 may be coupled to a portion of the sample introduction device 238 at a point upstream of the column inlet 252. The carrier gas may be any gas suitable for serving as an inert mobile phase that facilitates transport of the sample through the column 246 as appreciated by persons skilled in the art. Examples of carrier gases include, but are not limited to, helium, nitrogen, argon, and hydrogen. The flow of the carrier gas may be controlled by any means, such as a gas flow controller 268. In the illustrated example, the carrier gas is supplied to the column 246 via a carrier gas path that runs from the carrier gas source 242, through the carrier gas line 264 to the flow controller 268, and into the column inlet 252.

The heating device 250 may have any configuration suitable for maintaining the column 246 at a desired temperature setting or for varying the temperature of the column 246 according to a desired (i.e., predetermined) temperature profile (or temperature program). In one example, the GC housing 234 is (or contains) an oven, and the heating device 250 is configured for heating the interior of the oven through which the column 246 extends. In another example, the heating device 250 is configured for heating the column 246 directly. For instance, the heating device 250 may include a resistive heating element mounted in thermal contact with the column 246.

In addition to interfacing with components of the mass spectrometer 104 and the conditioning gas system 108, the system controller 168 may be configured for controlling and/or monitoring various aspects of the GC 230, such as sample introduction into the column 246, column leakage events, pressure settings, temperature settings or varying temperature profiles implemented by the heating device 250, and so on. For these purposes, the system controller 168 is schematically illustrated as being in signal communication with the GC 230 via a communication link 318, which may be wired or wireless and may represent one or more dedicated communication links to individual components of the GC 230. It can be seen that the system controller 168 schematically depicted in FIG. 1 may represent one or more modules, units, or devices for coordinating or synchronizing the various operations of the mass spectrometer 104 and the GC 230, as well as the conditioning gas system 108.

The MS system 100 is configured for operating in either an analytical mode or a conditioning mode, and for switching between the analytical mode and the conditioning mode. In the analytical mode, the sample is introduced into the ionization chamber 136 and the ionization device 140 operated to produce analyte ions from the sample. The analyte ions are transported into the mass analyzer 124, which sorts the ions according to mass. The resulting mass-discriminated ions are then transported to the ion detector 128, which is typically configured to convert the ion currents into electrical signals. The electrical signals are transmitted to a data analyzer, schematically represented by the system controller 168, for processing and generation of a mass spectrum or chromatogram.

In the conditioning mode, the MS system 100 is operated to flow a conditioning gas into the ionization chamber 136 via a conditioning gas flow path as described above. The effectiveness of the conditioning gas is optimized by adding energy to the conditioning gas to ionize the conditioning gas molecules. For this purpose, the ionization device 140 is operated to produce electrons or photons that interact with the conditioning gas molecules.

In some embodiments, the effectiveness of the conditioning gas may be further optimized by adding thermal energy to the conditioning gas and/or controlling its temperature. Temperature control may be accomplished by operating the heating system 164, which may be controlled by the system controller 168 and may follow a programmed temperature profile. In one example, the MS system 100 is configured for maintaining the ionization chamber 136 at a temperature ranging from ambient or room temperature to about 450° C.

The MS system 100 also may be configured for evaluating one or more parameters of the MS system 100 and, based on the value of the parameter, determining whether the MS system 100 should be operated in the conditioning mode (or, equivalently, should be switched from the analytical mode to the conditioning mode). Examples of parameters that may be evaluated include, but are not limited to, the number of times the MS system 100 or a component thereof (e.g., mass spectrometer 104, ion source 120, column 246) has been operated in the analytical mode prior to evaluating the parameter (or since the last time the parameter was evaluated, or since the last time the conditioning mode was implemented); the amount of time that has elapsed prior to evaluating the parameter (or since the parameter was last evaluated, or since the conditioning mode was last implemented); a quality of a chromatogram (or mass spectrum) produced by the MS system under predetermined operating conditions; a measurement of an abundance of ions of one or more selected mass-to-charge ratios taken while operating in the analytical mode or conditioning mode; and/or the presence of stationary phase material separated from a stationary phase support of the column (i.e., evidence of column bleed). The quality of the chromatogram may include any metric (e.g., signal-to-noise ratio) indicative of a degradation in signal response or other performance criterion of the MS system 100. Parameters such as the quality of the chromatogram and abundance of contaminant ions may be compared to reference parameters stored in the database 180 of the system controller 168 to assist in the determination as to whether the conditioning mode should be run. Measurements of the abundance of selected ions may be done while operating in the conditioning mode to enable adjustment of certain operating parameters of the conditioning mode, such as the level of conditioning gas being added. The evaluation of one or more parameters of the MS system 100 for the purpose of determining whether to operate in the conditioning mode may be performed or managed by the performance evaluator 188 of the system controller 168.

Alternatively or additionally, one or more of the above parameters may be evaluated manually by a user of the MS system 100. As examples, the user may keep track of the age and/or number of uses of the ion source 120. The user may make a visual inspection of a chromatogram or mass spectrum obtained from a sample analysis or a background analysis, and determine that the ion source 120 needs to be conditioned. Alternatively or additionally, the MS system 100 may be configured to enable the user to switch the MS system 100 to the conditioning mode at any desired time, or in accordance with a predetermined maintenance schedule.

If a determination is made that the MS system 100 should be operated in the conditioning mode, the MS system 100 may be configured for taking an action based on (or in response to) that determination. As examples, the action may include switching the operation of the MS system 100 to the conditioning mode, scheduling a time for switching the operation of the MS system 100 to the conditioning mode, modifying a pre-scheduled time for switching the operation of the MS system 100 to the conditioning mode, and/or producing a user-interpretable indication that the MS system 100 should be operated in the conditioning mode. A user-interpretable indication may include, for example, an audible or visual alarm, a visual indication or message displayed on a user control panel of the MS system 100 or on a display screen communicating with the MS system 100, an electronic mail or text message sent to a user, etc.

An example of a method for operating a mass spectrometry (MS) system will now be described with reference to the flow diagram of FIG. 2. The method includes flowing a first conditioning gas into an ion source of the MS system without introducing a sample into the ion source, and ionizing the first conditioning gas, wherein the ion source is conditioned by the first conditioning gas (step 202). The method further includes, after flowing the first conditioning gas, flowing a second conditioning gas into the ion source without introducing a sample into the ion source, and ionizing the second conditioning gas, wherein the ion source is conditioned by the second conditioning gas (step 204). The conditioning gases are ionized by operating the ionization device of the ion source. The method may further include, after flowing the second conditioning gas, resuming normal operation of the MS system such as analyzing a sample by introducing the sample into the conditioned ion source and collecting analytical data from the sample (step 206).

In an embodiment, the flowing of different conditioning gases (e.g., the first conditioning gas and then the second conditioning gas) into the ion source is done sequentially in distinct steps. For example, the first conditioning gas may be fed into the ion source at a desired (first) set-point flow rate. Once the first flow rate and temperature in the ion source have stabilized (i.e., reached a steady or equilibrium state), the first conditioning gas may continue to be fed at a constant flow rate for a desired (first) duration of time. Subsequently, flow of the first conditioning gas may be shut off. After stopping the flow of the first conditioning gas, the flow of the second conditioning gas may be initiated at a desired (second) set-point flow rate, which may or may not be different from the first set-point flow rate. Once the second flow rate and temperature in the ion source have stabilized, the second conditioning gas may continue to be fed at a constant flow rate for a desired (second) duration of time, which may or may not be different than the first duration of time over which the first conditioning gas was fed into ion source. Moreover, the temperature at which the second conditioning gas is regulated may or may not be different from the temperature at which the first conditioning gas was regulated.

In some embodiments, the sample may be introduced with a carrier gas, such as from a GC column. The carrier gas may be different from the first conditioning gas and the second conditioning gas.

In an embodiment, the first conditioning gas is primarily (or substantially) hydrogen gas. That is, the first conditioning gas has a composition comprising at least 90% (90% or greater, or 90% to 100%) hydrogen gas by volume. Thus, the first conditioning gas may be exclusively (purely) hydrogen gas, or may be a mixture of hydrogen gas and one or more other gases. In this embodiment, the second conditioning gas is primarily (or substantially) not hydrogen gas. That is, the second conditioning gas has a composition comprising less than 90% (from 0% to less than 90%) hydrogen gas by volume. The second conditioning gas may be a single gas or may be a mixture of two or more different gases. The gas or gases constituting the second conditioning gas may be one or more of the conditioning gases noted earlier in the present disclosure such as, for example, a hydrocarbon.

In another embodiment, the first conditioning gas has a composition comprising less than 90% (from 0% to less than 90%) hydrogen gas by volume, and the second conditioning gas also has a composition comprising less than 90% (from 0% to less than 90%) hydrogen gas by volume, but is different from the first conditioning gas. That is, the first and second conditioning gases are different compounds or different mixtures of compounds. The sample may be introduced into the ion source with a carrier gas, which may have a composition comprising at least 90% (90% or greater, or 90% to 100%) hydrogen gas by volume.

After flowing the second conditioning gas, the method may include repeating the steps of flowing the first conditioning gas into the ion source and ionizing the first conditioning gas. After repeating these steps, the method may further include repeating the steps of flowing the second conditioning gas into the ion source and ionizing the second conditioning gas. Thus, multiple iterations of the conditioning process may be performed prior to running a sample through the MS.

The method may include flowing one or more additional gases into the ion source. For example, after flowing the second conditioning gas, a third conditioning gas may be flowed into the ion source without introducing a sample into the ion source and ionized, wherein the ion source is further conditioned by the third conditioning gas. Depending on the embodiment, the composition of the third conditioning gas may be hydrogen (or primarily hydrogen) or not hydrogen (or primarily not hydrogen), and may be different from the second conditioning gas or from both the first conditioning gas and the second conditioning gas.

The MS system may be run in the normal, analytical mode prior to switching to the conditioning mode, i.e., a sample may be analyzed before flowing the first conditioning gas into the ion source. This sample may be referred to as a "first" sample, relative to the "second" sample that is analyzed after conditioning the ion source (i.e., flowing the first conditioning gas and the second conditioning gas into the ion source). Thus, before flowing the first conditioning gas into the ion source, the first sample may be analyzed by introducing the first sample into the ionization chamber and collecting analytical data from the first sample. In some embodiments, the first sample may be introduced into the ion source by flowing the first sample with a carrier gas into the ion source. In some embodiments, the first carrier gas is exclusively or primarily hydrogen gas.

In some embodiments, the method may include heating the first conditioning gas and/or the second conditioning gas, as described above.

In some embodiments, the method may include evaluating a parameter of the MS system and, based on evaluating the parameter, determining whether the MS system should be operated in the conditioning mode, for example determining whether the MS system should be switched from the analytical mode to the conditioning mode. As described above, a number of parameters may be considered. If it is determined that the MS system should be operated in the conditioning mode, the method may include taking one or more further actions in response, as described above.

Figure 2:
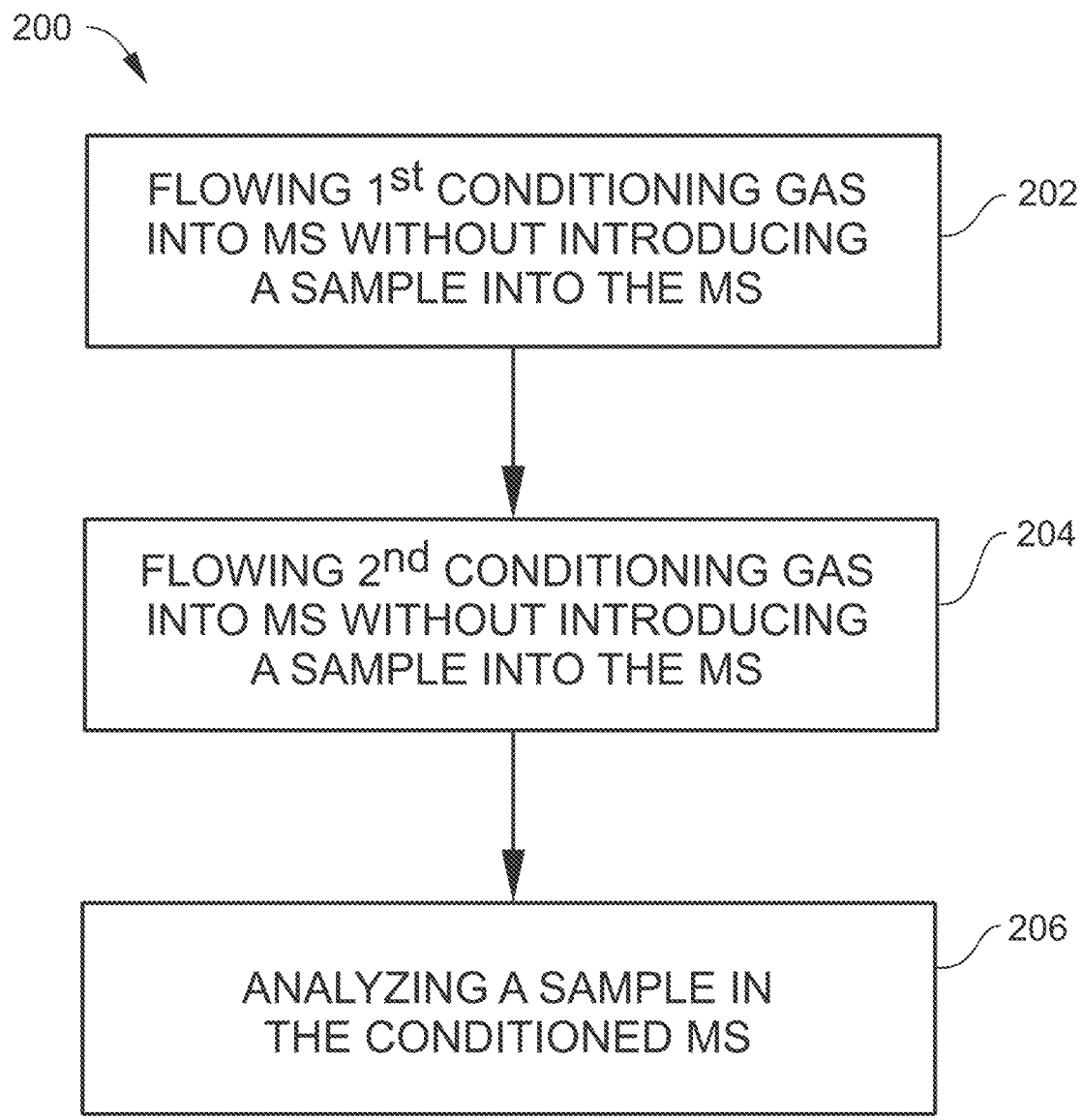
FIG. 2 is a flow diagram illustrating an example of a method for operating a mass spectrometry (MS) system according to an embodiment of the present disclosure.

According to an embodiment, FIG. 2 is also representative of an MS system configured for performing the method described herein. For example, the MS system may include components, such as those described above and illustrated in FIG. 1, configured for performing the steps illustrated in FIG. 2 and/or all or part of any of the methods disclosed herein.

According to an embodiment, a non-transitory computer-readable medium is provided. The non-transitory computer-readable medium includes instructions stored thereon, that when executed on a processor, control or perform the steps illustrated in FIG. 2 and/or all or part of any of the methods disclosed herein. For example, the system controller 168 of, or associated with, the MS system 100 described above and illustrated in FIG. 1 may be configured to read the non-transitory computer-readable medium and execute the instructions stored thereon.

Figure 3:
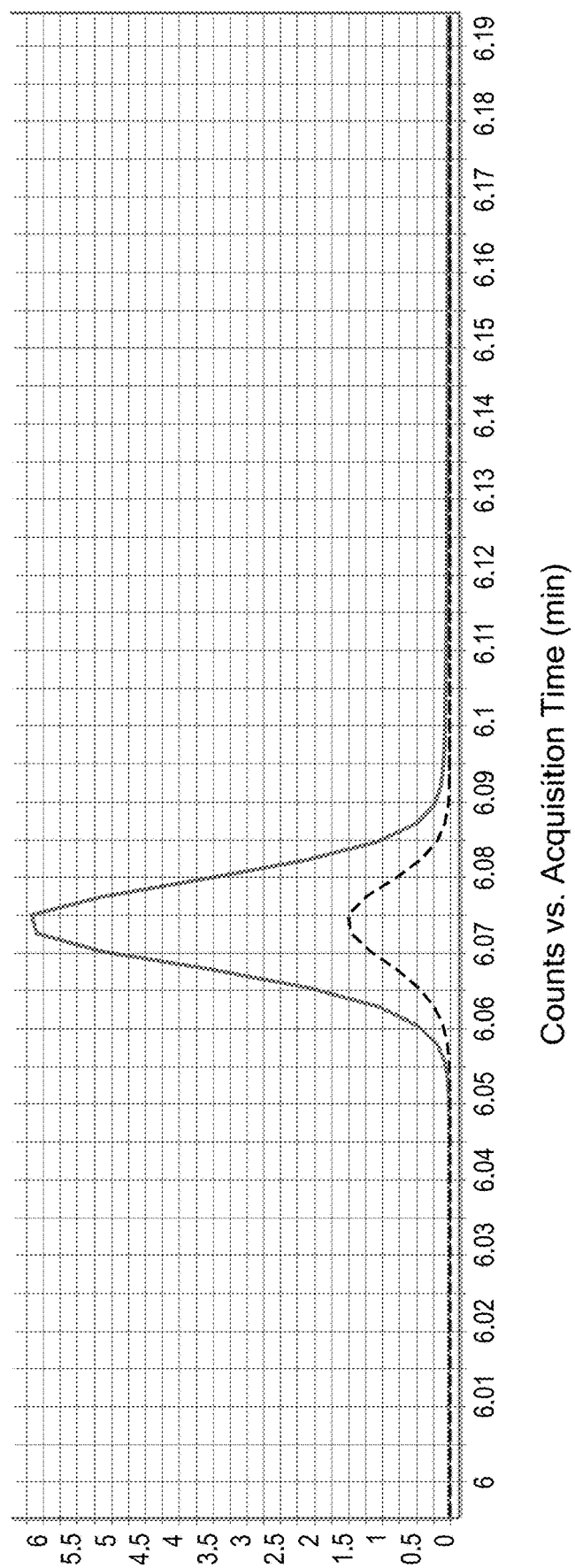
FIG. 3 is a total ion chromatogram (TIC) of selected ion monitoring (SIM) acquisitions for fenitrothion (O,O-Dimethyl O-(3-methyl-4-nitrophenyl)phosphorothioate) after various in situ conditioning processes implemented according to the present disclosure.

FIG. 3 is a total ion chromatogram (TIC) of selected ion monitoring (SIM) acquisitions for fenitrothion (O,O-Dimethyl O-(3-methyl-4-nitrophenyl)phosphorothioate) after various in situ conditioning processes implemented according to the present disclosure. The dashed line indicates the resulting ion source response after treating the ion source with hydrogen. The solid line indicates the resulting ion source response after treating the ion source with a hydrocarbon vapor (methane in this example) subsequent to the treatment with hydrogen, which produced a significantly larger peak in comparison to treatment by hydrogen alone.

FIG. 3 demonstrates that a two-step treatment utilizing two different conditioning gases can be more effective than a one-step treatment utilizing, for example, hydrogen.

Figure 4:
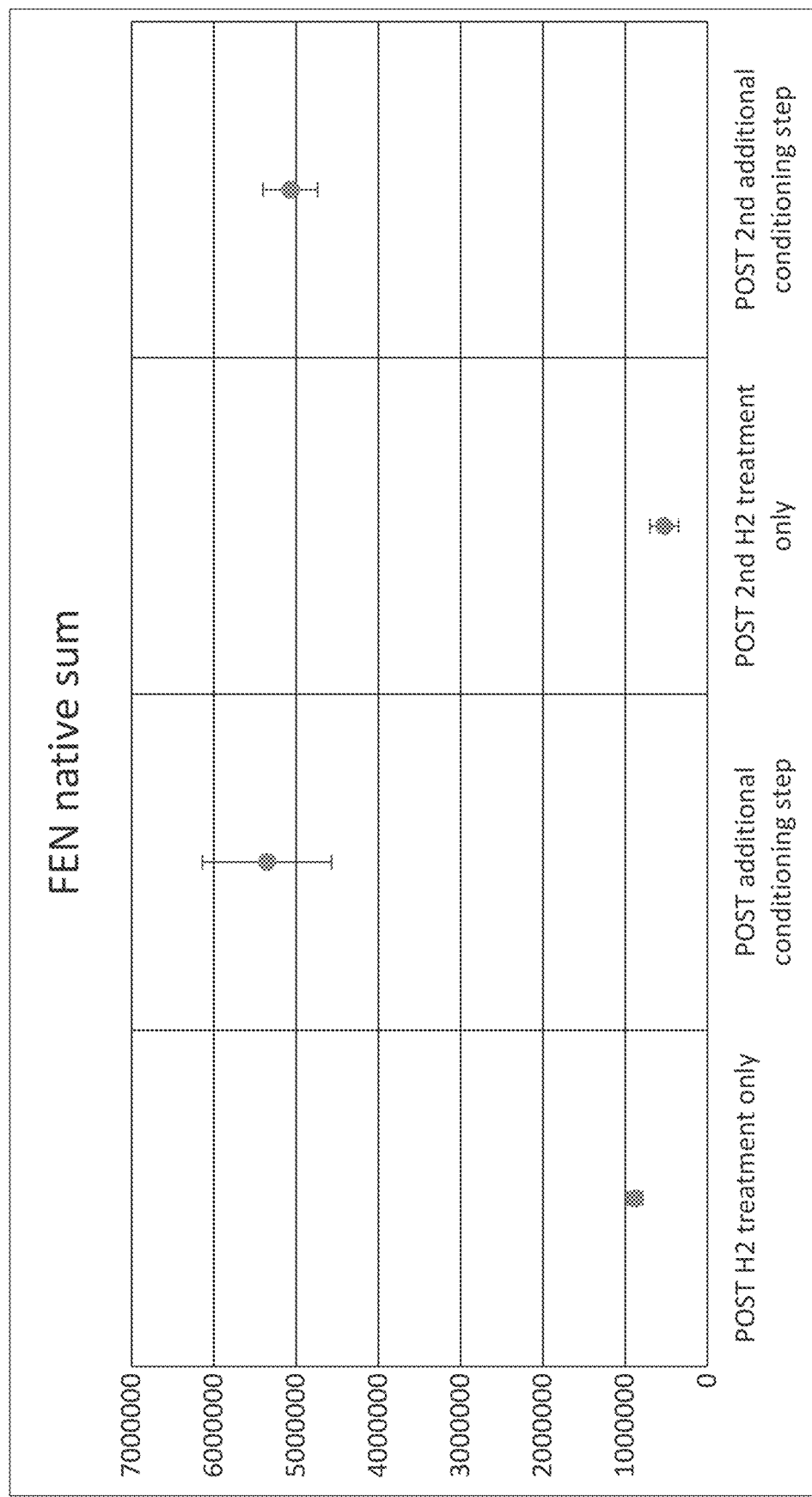
FIG. 4 is a set of average responses (ion detector counts) for fenitrothion resulting from alternating hydrogen conditioning and secondary conditioning processes, according to the present disclosure.

FIG. 4 is a set of average responses (ion detector counts) for fenitrothion resulting from alternating hydrogen conditioning and secondary conditioning processes, according to the present disclosure. The horizontal axis is divided into four regions corresponding to four successive treatment steps, specifically from left to right: (1) treatment by hydrogen, (2) treatment by a hydrocarbon vapor (methane in this example), (3) an additional treatment by hydrogen, and (4) an additional treatment by a hydrocarbon vapor (methane in this example). As shown, the response significantly increased after the first treatment by the hydrocarbon in comparison to treatment by hydrogen alone. After the second treatment by hydrogen, the response decreased. However, after the second treatment by the hydrocarbon, the response again increased.

From the foregoing, it can be seen the embodiments described herein may eliminate—or significantly lower the frequency of—conventional MS servicing tasks, such as removal, ex situ cleaning, and re-installation of contaminated parts, and restore or improve the performance of an MS system. Application of an off-line conditioning process as described herein may rapidly improve the background of the MS system, including with respect to chemically adsorbed species such as water which otherwise would have a very slow rate of elimination, and species such as the solvents or hydrocarbons adsorbed on MS components upon exposure to air during conventional cleaning.

Exemplary Embodiments

Exemplary embodiments provided in accordance with the presently disclosed subject matter include, but are not limited to, the following:

1. A method for operating a mass spectrometry (MS) system, the method comprising: flowing a first conditioning gas into an ion source of the MS system without introducing a sample into the ion source; ionizing the first conditioning gas, wherein the ion source is conditioned by the first conditioning gas; after flowing the first conditioning gas, flowing a second conditioning gas into the ion source without introducing a sample into the ion source; ionizing the second conditioning gas, wherein the ion source is conditioned by the second conditioning gas; and after flowing the second conditioning gas, analyzing a sample by introducing the sample into the conditioned ion source and collecting analytical data from the sample, wherein: the first conditioning gas has a composition comprising at least 90% hydrogen gas by volume; and the second conditioning gas has a composition comprising from 0% to less than 90% hydrogen gas by volume.

2. The method of embodiment 1, wherein the second conditioning gas comprises a compound selected from the group consisting of: a hydrocarbon; ammonia; methylamine; a ketone; an alcohol; acetonitrile; silane; a silane derivative; and a combination of two or more of the foregoing.

3. The method of embodiment 1, wherein the second conditioning gas comprises a compound selected from the group consisting of: methane; butane; isobutane; pentane; hexane; toluene; benzene; xylene; and a combination of two or more of the foregoing.

4. The method of embodiment 1, wherein the second conditioning gas comprises a compound selected from the group consisting of: acetone; methanol; ethanol; and a combination of two or more of the foregoing.

5. The method of any of the preceding embodiments, wherein the first conditioning gas and the second conditioning gas have a composition selected from the group consisting of: the first conditioning gas is a mixture of two or more different gases; the second conditioning gas is a mixture of two or more different gases; and both of the foregoing.

6. The method of any of the preceding embodiments, comprising, after flowing the second conditioning gas, repeating the step of flowing the first conditioning gas into the ion source.

7. The method of any of embodiments 1-5, comprising, after flowing the second conditioning gas, repeating the steps of flowing the first conditioning gas and the second conditioning gas into the ion source.

8. The method of any of the preceding embodiments, comprising, after flowing the second conditioning gas, flowing a third conditioning gas into the ion source without introducing a sample into the ion source, and ionizing the third conditioning gas, wherein the ion source is conditioned by the third conditioning gas, the third conditioning gas has a composition comprising from 0% to less than 90% hydrogen gas by volume, and the third conditioning gas is different from the second conditioning gas.

9. The method of any of the preceding embodiments, wherein introducing the sample comprises flowing the sample with a carrier gas into the conditioned ion source.

10. The method of embodiment 9, wherein the carrier gas is different from the first conditioning gas and the second conditioning gas.

11. The method of any of the preceding embodiments, wherein the sample introduced after flowing the second conditioning gas is a second sample, and further comprising: before flowing the first conditioning gas into the ion source, analyzing a first sample by introducing the first sample into the ion source and collecting analytical data from the first sample.

12. The method of embodiment 11, wherein introducing the first sample comprises flowing the first sample with a carrier gas into the ion source.

13. The method of any of the preceding embodiments, comprising, while flowing at least one of the first conditioning gas or the second conditioning gas into the mass spectrometer, heating the at least one of the first conditioning gas or the second conditioning gas.

14. The method of any of the preceding embodiments, wherein ionizing the first conditioning gas and the second conditioning gas comprises irradiating the first conditioning gas and the second conditioning gas with electrons or photons.

15. A mass spectrometry (MS) system, configured for performing the method of any of the preceding embodiments.

16. A non-transitory computer-readable medium, comprising instructions stored thereon, that when executed on a processor, control or perform the steps of flowing the first conditioning gas, flowing the second conditioning gas, and analyzing the sample, according to the method of any of the preceding embodiments.

17. A mass spectrometry (MS) system, comprising the non-transitory computer-readable medium of embodiment 16.

18. A method for operating a mass spectrometry (MS) system, the method comprising: flowing a first conditioning gas into an ion source of the MS system without introducing a sample into the ion source; ionizing the first conditioning gas, wherein the ion source is conditioned by the first conditioning gas; after flowing the first conditioning gas, flowing a second conditioning gas into the ion source without introducing a sample into the ion source; ionizing the second conditioning gas, wherein the ion source is conditioned by the second conditioning gas; and after flowing the second conditioning gas, analyzing a sample by introducing the sample with a carrier gas into the conditioned ion source and collecting analytical data from the sample, wherein: the carrier gas has a composition comprising at least 90% hydrogen gas by volume; the first conditioning gas has a composition comprising from 0% to less than 90% hydrogen gas by volume; and the second conditioning gas has a composition comprising from 0% to less than 90% hydrogen gas by volume, and is different from the first conditioning gas.

19. The method of embodiment 18, wherein the first conditioning gas and the second conditioning gas each comprise a compound selected from the group consisting of: a hydrocarbon; ammonia; methylamine; a ketone; an alcohol; acetonitrile; silane; a silane derivative; and a combination of two or more of the foregoing.

20. The method of embodiment 18, wherein the first conditioning gas and the second conditioning gas each comprise a compound selected from the group consisting of: methane; butane; isobutane; pentane; hexane; toluene; benzene; xylene; and a combination of two or more of the foregoing.

21. The method of embodiment 18, wherein the first conditioning gas and the second conditioning gas each comprise a compound selected from the group consisting of: acetone; methanol; ethanol; and a combination of two or more of the foregoing.

22. The method of any of embodiments 18-21, comprising, after flowing the second conditioning gas, flowing a third conditioning gas into the mass spectrometer without introducing a sample into the mass spectrometer, wherein the mass spectrometer is conditioned by the third conditioning gas, the third conditioning gas has a composition comprising from 0% to less than 90% hydrogen gas by volume, and the third conditioning gas is different from the second conditioning gas and from the carrier gas.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 168 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 168 in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for operating a mass spectrometry (MS) system, the method comprising:
conditioning an ion source of the MS system to improve an analyte signal response of the MS system, by:
flowing a first conditioning gas into the ion source without introducing a sample into the ion source;
ionizing the first conditioning gas, wherein the ion source is conditioned by the first conditioning gas;
stopping the flowing of the first conditioning gas;
after stopping the flowing of the first conditioning gas, flowing a second conditioning gas into the ion source without introducing a sample into the ion source; and
ionizing the second conditioning gas, wherein the ion source is conditioned by the second conditioning gas; and
after flowing the second conditioning gas, analyzing a sample by introducing the sample into the conditioned ion source, producing analyte ions from the sample, and collecting analytical data from the sample, wherein:
the first conditioning gas has a composition comprising at least 90% hydrogen gas by volume; and
the second conditioning gas has a composition comprising from 0% to less than 90% hydrogen gas by volume.

2. The method of claim 1, wherein the second conditioning gas comprises a compound selected from the group consisting of: a hydrocarbon; ammonia; methylamine; a ketone; an alcohol; acetonitrile; silane; a silane derivative; and a combination of two or more of the foregoing.

3. The method of claim 1, wherein the second conditioning gas comprises a compound selected from the group consisting of: methane; butane; isobutane; pentane; hexane; toluene; benzene; xylene; and a combination of two or more of the foregoing.

4. The method of claim 1, wherein the second conditioning gas comprises a compound selected from the group consisting of: acetone; methanol; ethanol; and a combination of two or more of the foregoing.

5. The method of claim 1, wherein the first conditioning gas and the second conditioning gas have a composition selected from the group consisting of:
the first conditioning gas is a mixture of two or more different gases;
the second conditioning gas is a mixture of two or more different gases; and
both of the foregoing.

6. The method of claim 1, comprising, after flowing the second conditioning gas, repeating the step of flowing the first conditioning gas into the ion source.

7. The method of claim 1, comprising, after flowing the second conditioning gas, repeating the steps of flowing the first conditioning gas and the second conditioning gas into the ion source.

8. The method of claim 1, comprising, after flowing the second conditioning gas, flowing a third conditioning gas into the ion source without introducing a sample into the ion source, and ionizing the third conditioning gas, wherein the ion source is conditioned by the third conditioning gas, the third conditioning gas has a composition comprising from 0% to less than 90% hydrogen gas by volume, and the third conditioning gas is different from the second conditioning gas.

9. The method of claim 1, wherein introducing the sample comprises flowing the sample with a carrier gas into the conditioned ion source.

10. The method of claim 9, wherein the carrier gas is different from the first conditioning gas and the second conditioning gas.

11. The method of claim 1, wherein the sample introduced after flowing the second conditioning gas is a second sample, and further comprising:
before flowing the first conditioning gas into the ion source, analyzing a first sample by introducing the first sample into the ion source and collecting analytical data from the first sample.

12. The method of claim 11, wherein introducing the first sample comprises flowing the first sample with a carrier gas into the ion source.

13. The method of claim 1, comprising, while flowing at least one of the first conditioning gas or the second conditioning gas into the mass spectrometer, heating the at least one of the first conditioning gas or the second conditioning gas.

14. The method of claim 1, wherein ionizing the first conditioning gas and the second conditioning gas comprises irradiating the first conditioning gas and the second conditioning gas with electrons or photons.

15. A mass spectrometry (MS) system, configured for performing the method of claim 1.

16. A non-transitory computer-readable medium, comprising instructions stored thereon, that when executed on a processor, control or perform the steps of flowing the first conditioning gas, flowing the second conditioning gas, and analyzing the sample, according to the method of claim 1.

17. A mass spectrometry (MS) system, comprising the non-transitory computer-readable medium of claim 16.

18. A method for operating a mass spectrometry (MS) system, the method comprising:
conditioning an ion source of the MS system to improve an analyte signal response of the MS system, by:
flowing a first conditioning gas into the ion source without introducing a sample into the ion source;
ionizing the first conditioning gas, wherein the ion source is conditioned by the first conditioning gas;
stopping the flowing of the first conditioning gas;
after stopping the flowing of the first conditioning gas, flowing a second conditioning gas into the ion source without introducing a sample into the ion source; and
ionizing the second conditioning gas, wherein the ion source is conditioned by the second conditioning gas; and
after flowing the second conditioning gas, analyzing a sample by introducing the sample with a carrier gas into the conditioned ion source, producing analyte ions from the sample, and collecting analytical data from the sample, wherein:
the carrier gas has a composition comprising at least 90% hydrogen gas by volume;
the first conditioning gas has a composition comprising from 0% to less than 90% hydrogen gas by volume; and
the second conditioning gas has a composition comprising from 0% to less than 90% hydrogen gas by volume, and is different from the first conditioning gas.

19. The method of claim 18, wherein the first conditioning gas and the second conditioning gas each comprise a compound selected from the group consisting of: a hydrocarbon; ammonia; methylamine; a ketone; an alcohol; acetonitrile; silane; a silane derivative; and a combination of two or more of the foregoing.

20. The method of claim 18, comprising, after flowing the second conditioning gas, flowing a third conditioning gas into the mass spectrometer without introducing a sample into the mass spectrometer, wherein the mass spectrometer is conditioned by the third conditioning gas, the third conditioning gas has a composition comprising from 0% to less than 90% hydrogen gas by volume, and the third conditioning gas is different from the second conditioning gas and from the carrier gas.

* * * * *